United States Patent [19]
Stine et al.

[11] Patent Number: 5,811,608
[45] Date of Patent: Sep. 22, 1998

[54] PROCESS FOR OLIGOMER PRODUCTION AND SATURATION

[75] Inventors: Laurence O. Stine, Western Springs; Brian S. Muldoon, Willowbrook; Steven C. Gimre, Carol Stream; Robert R. Frame, Glenview, all of Ill.

[73] Assignee: UOP LLC, Des Plaines, Ill.

[21] Appl. No.: 573,315

[22] Filed: Dec. 15, 1995

[51] Int. Cl.$^6$ .............................. C07C 2/74; C07C 5/03; C07C 2/18

[52] U.S. Cl. ................ 585/316; 585/254; 585/255; 585/310; 585/315; 585/324; 585/329; 585/330; 585/518; 585/529

[58] Field of Search ...................... 585/250, 254, 585/255, 310, 315, 316, 324, 329, 330, 514, 518, 520, 527, 529

[56] References Cited

U.S. PATENT DOCUMENTS

| | | | |
|---|---|---|---|
| 2,199,132 | 4/1940 | Hull | 585/316 |
| 2,526,966 | 10/1950 | Oberfell et al. | 196/1 |
| 4,200,714 | 4/1980 | Mahoney et al. | 526/68 |
| 4,254,294 | 3/1981 | Juguin et al. | 585/525 |
| 4,304,948 | 12/1981 | Vora et al. | 585/315 |
| 4,393,259 | 7/1983 | Ward et al. | 585/315 |
| 4,678,645 | 7/1987 | Chang et al. | 585/330 |
| 4,749,820 | 6/1988 | Kuo et al. | 585/330 |
| 5,049,360 | 9/1991 | Harandi et al. | 422/141 |

FOREIGN PATENT DOCUMENTS

| | | |
|---|---|---|
| 2186287 | 2/1987 | United Kingdom . |
| 2186287 | 8/1987 | United Kingdom . |

*Primary Examiner*—Glenn Caldarola
*Assistant Examiner*—Thuan D. Dang
*Attorney, Agent, or Firm*—Thomas K. McBride; John G. Tolomei

[57] ABSTRACT

A process for the production of saturated oligomers by the oligomerization of light olefins to heavier olefins and the saturation of the heavy olefins is improved by the recycle of the heavy paraffins to the oligomerization zone. The recycle of the heavy paraffins improves the selectivity of the oligomerization for $C_8$ paraffin products and reduces catalyst fouling. The reduced catalyst fouling can be used to operate the oligomerization zone at lower pressure and facilitate its integration with a dehydrogenation zone for the production of the light olefin stream.

22 Claims, 1 Drawing Sheet

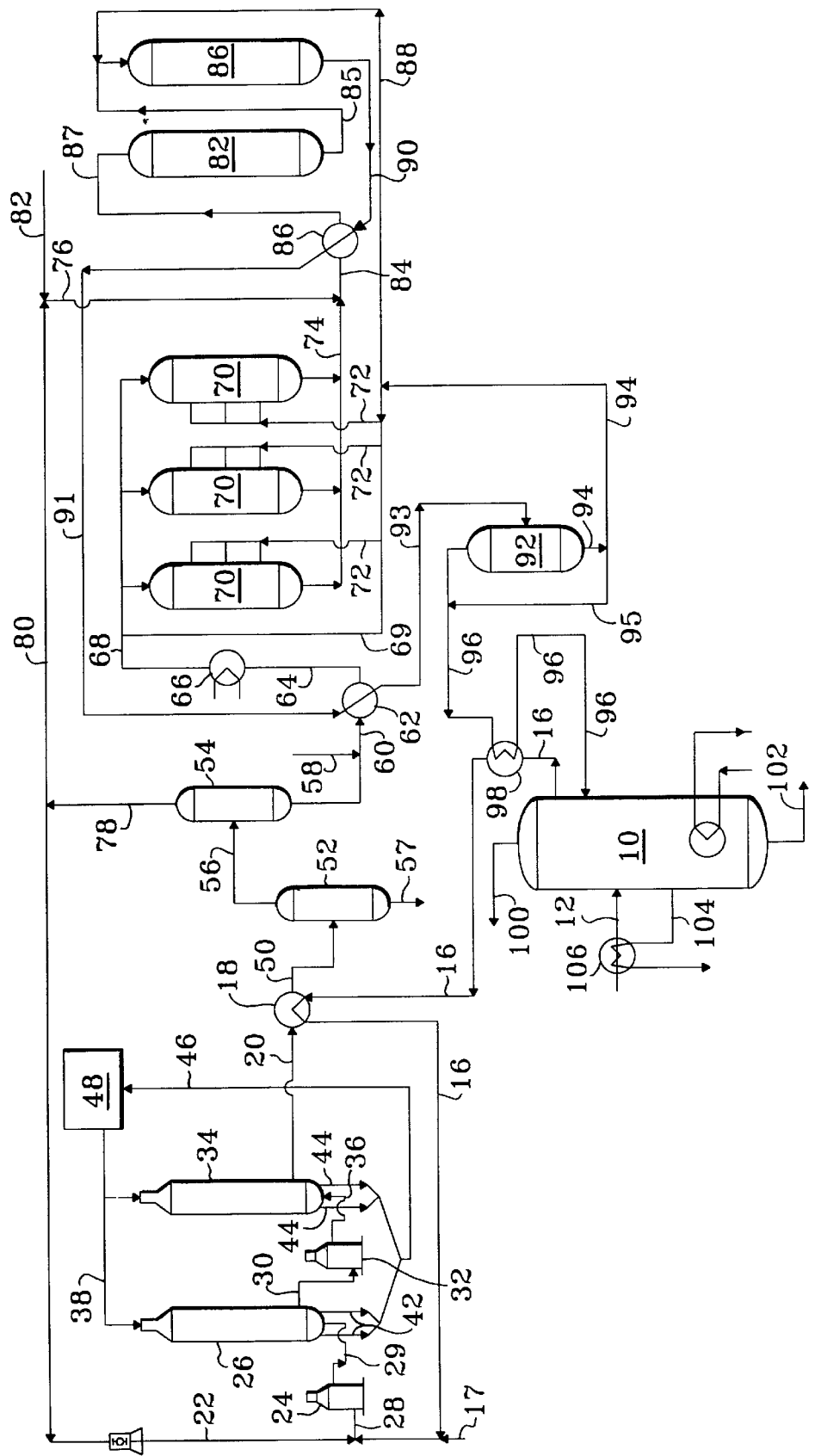

PROCESS FOR OLIGOMER PRODUCTION AND SATURATION

FIELD OF THE INVENTION

This invention relates generally to the production of gasoline boiling range hydrocarbons by the oligomerization of light olefins and the saturation of the resulting heavier olefins.

BACKGROUND OF THE INVENTION

PRIOR ART

A continuing demand exists for the conversion of light hydrocarbons into high octane motor fuels. The alkylation of isobutane with propylene, butenes and amylenes using a hydrofluoric acid (HF) catalyst, commonly referred to as HF alkylation, has provided a highly successful method for the production of high octane motor fuels. Despite a long history of safe operation, recent concerns over the possibility of a catastrophic release of HF acid from HF alkylation units has prompted the investigation of modification or alternatives to the HF alkylation process for the production of motor fuels. One existing alternative is a similar alkylation process that uses sulfuric acid as the catalyst. While the use of sulfuric acid may decrease the degree of the hazard that some associate with the use of HF acid, the sulfuric acid process is still perceived as possibly presenting the same hazard and is not as economically advantageous as the HF alkylation process. Therefore, processing substitutes for the HF alkylation process are still sought.

Other methods of combining isobutane with light olefins to produce motor fuels are known and practiced but, do not produce the same quality gasoline products or are more expensive to install and operate. One such alternative is the dehydrogenation of isobutane and the oligomerization of the resulting olefins to produce gasoline boiling range hydrocarbons. The oligomerization of light olefins into higher molecular weight motor fuels using a solid phosphoric acid is well known and its use predates the HF alkylation process. Such oligomerization processes are also referred to as catalytic condensation and polymerization with the resulting motor fuel often referred to as polymer gasoline. Patents disclosing the dehydrogenation of light paraffin stream with oligomerization of the dehydrogenation effluent include U.S. Pat. Nos. 4,393,259, 5,049,360, 4,749,820, 4,304,948 and 2,526,966.

It also known to hydrotreat the olefinic hydrocarbon streams produced by oligomerization to saturate olefins. Patent GB 2186287 discloses dehydrogenation of and oligomerization of a C4 fraction to produce a jet aircraft fuel that is optionally hydrogenated into premium gasoline. The hydrotreatment of jet fuels, diesel fuels and lubes produced by dehydrogenation and oligomerization of light paraffins is disclosed in U.S. Pat. No. 4,678,645. However, hydrotreating is not always beneficial for gasoline fractions produced by oligomerization and can lower octane ratings, but is known to be particularly beneficial when saturating isooctenes to isooctanes.

It is an object of this invention to improve the integrated operation of an oligomerization zone and a saturation zone.

It is a further object of this invention to provide improved integration of an oligomerization zone and saturation zone that, in combination with a dehydrogenation zone, can provide an alternative to HF alkylation.

BRIEF SUMMARY OF THE INVENTION

This invention integrates the oligomerization of light olefins with the saturation of the resulting oligomers by recycling a portion of the saturated oligomers as a recycle to the oligomerization zone. The recycle of saturated oligomers to the oligomerization zone will inhibit fouling of the oligomerization zone catalyst by the deposition of coke while surprisingly also providing improvements in the selectivity of the oligomerization zone to higher octane $C_8$ isomers. The reduced fouling promoted by the recycle of heavy paraffins from the saturated oligomerization effluent can be used to extend catalyst life with the oligomerization zone or to operate the oligomerization zone at lower pressure.

Operation at lower pressure is particularly beneficial when the oligomerization zone and saturation zone are integrated with a dehydrogenation zone to provide a source of light olefin feed. The typically low pressure operation of the dehydrogenation is more efficiently integrated with the oligomerization zone as its operating pressure decreases. Operating pressures for the dehydrogenation reactor can range from 5 to 150 psig while operating pressures for a typical oligomerization zone will normally exceed 300 psig and will often be about 500 psig. By recycling saturated oligomers to reduce fouling oligomerization zone pressures may consistently drop below 300 psig. The operating pressure differential between the dehydrogenation zone and the oligomerization zone may shrink to less than 150 psig and eliminate the need for any dual stage compression between the zones. Thus an integrated dehydrogenation, oligomerization and saturation zone arrangement benefits from recycle by both improved selectivity and operational costs.

Accordingly in a broad embodiment this invention is a process for the production of saturated oligomers. The process passes an oligomerization zone feed comprising $C_3$ to $C_5$ olefins at oligomerization conditions into contact with an oligomerization catalyst at oligomerization conditions including a temperature of 200° to 500° F., a pressure of 100 to 1000 psig, and an LHSV of 0.5 to 5. A recycle stream comprising $C_7$ and heavier paraffins passes into contact with the catalyst and an oligomerization effluent stream comprising $C_7$ and heavier olefins and paraffins is recovered from the oligomerization zone. At least a portion of the effluent from the oligomerization zone and a hydrogen containing stream are passed into a saturation zone and contacted with a saturation catalyst at saturation conditions to saturate olefins in the oligomerization effluent. At least a portion of the saturation zone effluent stream comprising paraffinic hydrocarbons having at least 7 carbon atoms is passed to said oligomerization zone as said recycle stream while a portion of the saturation zone effluent stream comprising $C_8$ and heavier paraffins is recovered.

In a more specific embodiment this invention is process for the production of a motor fuel product from an isobutane containing input stream. The process passes an input stream comprising isobutane to a dehydrogenation zone and contacts the input stream in the dehydrogenation zone with a dehydrogenation catalyst at dehydrogenation conditions including a temperature of 950° to 1200° F., a pressure of 5 to 150 psig and an LHSV of 0.5–50 and recovers hydrogen and a dehydrogenation effluent comprising C4 isoolefins from the dehydrogenation zone. After separating a hydrogen stream from the dehydrogenation zone effluent at a hydrogen purity of from 70–95 mol %, the remainder of the dehydrogenation zone effluent passes to an oligomerization zone as a liquid phase feed stream comprising $C_4$ olefins. In the oligomerization zone the oligomerization zone feed and a recycle stream contacts a solid oligomerization catalyst at oligomerization conditions including a temperature of 200° to 500° F., a pressure of 100 to 300 psig, and an LHSV of 0.5 to 5 to recover an oligomerization effluent comprising $C_7$ and higher isoolefins. Effluent from the oligomerization zone passes without separation into a saturation zone along with the hydrogen stream. The saturation zone contacts the oligomerization zone effluent and hydrogen with a saturation catalyst at saturation conditions to saturate olefins in the oligomerization effluent. At least a portion of the saturation zone effluent stream passes to a separation zone to recover a saturated stream comprising $C_7$ and heavier paraffins. At least a portion of the recovered saturated stream passes to said oligomerization zone as said recycle stream.

Other objects, embodiments and details of this invention will be provided in the following detailed disclosure of the invention.

BRIEF DESCRIPTION OF THE DRAWINGS

The figure is a schematic process flow diagram of the invention showing principal processing zones and related piping and equipment.

DETAILED DESCRIPTION OF THE INVENTION

The essential operational zone for the practice of this invention is the oligomerization reaction zone. Suitable oligomerization zones for this invention take on many forms. The oligomerization process is known by many names such as catalytic condensation and also catalytic polymerization. Known catalysts for effecting such reactions include solid phosphoric acid catalysts known as SPA catalysts and homogenous catalysts such as borontrifluoride as described in U.S. Pat. Nos. 3,906,053, 3,916,019 and 3,981,941.

The preferred catalyst for the oligomerization process is the solid phosphoric acid (SPA) catalyst. The SPA catalyst as previously mentioned refers to a solid catalyst that contains as a principal ingredient an acid of phosphorous such as ortho-, pyro- or tetraphosphoric acid. The catalyst is normally formed by mixing the acid of phosphorous with a siliceous solid carrier to form a wet paste. This paste may be calcined and then crushed to yield catalyst particles where the paste may be extruded or pelleted prior to calcining to produce more uniform catalyst particles. The carrier is preferably a naturally occurring porous silica-containing material such as kieselguhr, kaolin, infusorial earth, and diatomaceous earth. A minor amount of various additives such as mineral talc, fuller's earth, and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this composition such as a lower phosphoric acid content are however possible. Further details as to the composition and production of SPA catalysts may be obtained from U.S. Pat. Nos. 3,050,472; 3,050,473, and 3,132,109 and from other references.

Oligomerization zones in general are maintained at conditions which may vary widely due to the previously listed variables. In this invention the oligomerization reaction zone is preferably operated at temperatures and pressures that increase the compatibility of its effluent conditions with the inlet conditions of the saturation reaction zone inlet and its inlet conditions with the dehydrogenation reaction zone effluent conditions. The preferred temperature of the oligomerization reaction zone will typically be in a range of from 100° to 500° F. and will more typically be in a range of from 300° to 450° F. with particularly preferred temperatures for some catalysts of from 300° to 400° F. Pressures within the oligomerization reaction zone will usually be in a range of from 100 to 1200 psig and more typically in a range of from 100 to 500 psig when using this invention to reduce the operating pressure of the oligomerization zone. When practicing this invention the preferred operating pressure for the SPA catalyst will be in a range of from 100 to 1000 psig with 100 to 300 psig being particularly preferred. It has also been found that maintaining operating temperatures in a narrow range of from 300° to 340° F. can have push selectivity toward the production of more $C_8$ isomers.

The feed to the oligomerization zone reaction will typically comprise $C_3$ to $C_5$ olefins and paraffins. Steam or water may be fed into the reactor to maintain a low water content for hydration of the preferred SPA catalyst. The source of the olefin feeds are typically a light gas stream recovered from the gas separation section of an FCC process, $C_4$ streams from steam cracking and coker off gas or the effluent from dehydrogenation zone. The olefin feed stream is characterized by having an overall $C_4$ olefin concentration of at least 10 wt %. In most operations, this olefin feed stream will contain $C_4$ olefins but it may also constitute all or substantial quantities of $C_3$ olefins. Typically the olefin feeds can have a $C_3$ to $C_5$ olefin concentration of at least 30 wt %. Preferred feeds will have a $C_4$ olefin concentration of at least 30 wt % and more preferably at least 50 wt %. Preferably the olefin feed stream will comprise at least 20 wt % and more preferably 30 wt % isobutene. The isobutene will preferably comprise at least 33% of the total butenes. The olefin content of preferred feeds will predominately comprise branched olefins with isobutene present in large quantities. The reaction of normal pentenes and propylene is promoted by maintaining a high concentration of isobutene in the feed to the oligomerization zone of this invention. Oligomerization of pentene and propylene into high octane isomers is promoted by having an olefin distribution in the feed to the isomerization zone that comprises at least 50 wt % isobutene. When large quantities of propylene are present in the feed to the oligomerization zone, the octane number of the product may be increased by raising the percentage of isobutene in the butene fraction of the feed. Preferably the butene fraction will comprise 100% isobutene when large amounts of propylene enter the oligomerization zone.

In the practice of this invention heavy paraffin components contact the catalyst in conjunction with the usual oligomerization zone feed. The heavy paraffin components will comprise hydrocarbons having at least seven carbon atoms and up to 20 carbon atoms and will preferably comprise $C_8$ to $C_{12}$ paraffins. Addition of a heavy paraffin stream will provide a substantial quantity of heavy paraffins in the oligomerization zone and preferably will produce a minimum of 20 wt % $C_7$ and heavier paraffins in the reactor effluent stream and will more typically produce at least 25 wt % of $C_8$ and heavier paraffins at the inlet of each catalyst bed. $C_8$ paraffins are particularly preferred and will preferably comprise 5 wt % as minimum to a first catalyst bed to as much as 50 wt % of the mass flow through the oligomerization reaction zone.

The heavy paraffin components may enter the process with the incoming feed or may be injected into an oligomerization reaction zone at intermediate locations. The different catalyst beds are preferably contained within one or more cylindrical, vertically oriented vessels and the feed stream preferably enters the top of the reactor. The catalyst is preferably disposed in fixed beds within the oligomerization zone in what is known as a chamber-type reactor structure. Typically, a chamber-type reactor will contain about five catalyst beds. In a chamber-type reactor, the reactants flow through a series of large diameter catalyst beds. The temperature of the reactants may be further controlled by recycling additional relatively inert hydrocarbons to act as a heat sink. Oligomerization reaction zones are routinely arranged with such multiple beds of catalyst that receive an intermediate injection of a quench material to control temperatures from the exothermic reaction. Substantial advantage can be obtained by adding the heavy paraffin feed as an intermediate injection stream that also benefits the process by serving as a quench stream.

With the addition of the heavy paraffin stream the combined feed to the oligomerization zone will preferably have a ratio of paraffins to olefins of from 1:1 to 5:1. Typically the paraffin concentration of the feed to the oligomerization reaction zone will be at least 50 wt % and more typically at least 70 wt %. A high percentage of the olefin in the feed stream are reacted in the oligomerization reaction zone along with the isobutene. The olefin conversion will typically range of from 80 to 99%. The principal oligomerization products comprise $C_7+$ olefins.

The oligomerization effluent containing the unreacted heavy paraffins and the resulting heavy olefinic hydrocarbons passes to the saturation reactor. Suitable saturation reactors provide an essentially complete saturation of all olefins from the saturation reactor. The effluent from the oligomerization zone will preferably pass directly to the saturation zone without separation or recovery of light ends. Lower pressure operation for the oligomerization reactor allows direct passage of the polymerization effluent to the hydrogenation reactor. Exothermicity will typically cause the saturation zone to operate at higher temperatures than the oligomerization zone so that quench fluid and paraffins in the effluent from the oligomerization will provide additional heat sink material for the heat release of the saturation reaction zone.

Before entering the saturation zone the oligomerization effluent is first mixed with a hydrogen containing gas stream. The gas stream should contain at least 50 wt % of hydrogen. Preferably, the hydrogen containing gas stream will have a hydrogen concentration greater than 75% wt % hydrogen. Hydrogen can be recovered from a dehydrogenation section to supply a major amount of the hydrogen input for the saturation zone with the remainder of the necessary hydrogen supplied from outside sources as a make-up hydrogen or where a dehydrogenation zone is not present, outside sources may supply all of the necessary hydrogen. High purity is preferred for the make-up hydrogen to increase the overall purity of the hydrogen entering the saturation zone thereby reducing the volume of light hydrocarbons. These light hydrocarbons are generally undesirable since their presence needlessly increases the mass volume through the saturation reaction zone and their relatively high vapor pressure can increase the loss of potential hydrocarbons in downstream separations. However, the arrangement of this invention in a preferred configuration that integrates dehydrogenation, oligomerization, and saturation may facilitate the use of separation arrangements that can accommodate low purity hydrogen streams.

The make-up gas stream is mixed with the oligomerization effluent in proportions that will produce a hydrogen to hydrocarbon ratio in a range of 0.1 to 2. and more preferably in a range of from 0.15 to 0.30.

The preferred saturation reactor of this invention will provide an essentially complete saturation of all unsaturated hydrocarbons. Conditions within the hydrotreating zone typically include a temperature in the range of 200°–600° F., a pressure of from 100 to 700 psig and a liquid hourly space velocity of from 1 to 20. Preferably, the reaction conditions are selected to keep the hydrocarbon feed in a vapor phase. The hydrotreater arrangement will generally operate at temperatures that permit the raising of the combined feed stream to saturation reaction temperatures by heat exchange with the hydrotreater effluent. In this manner any heat importation into the oligomerization and hydrogenation sequence can preferably be made by a trim heater on the inlet stream to the oligomerization reaction zone.

The preferred hydrotreatment reactor contains a fixed bed of hydrotreatment catalyst. Catalytic composites that can be used in this process include traditional hydrotreating catalysts. Combinations of clay and alumina-containing metallic elements from both Group VIII and Group VIB of the Periodic Table have been found to be particularly useful. Group VIII elements include iron, cobalt, nickel, ruthenium, rhenium, palladium, osmium, indium and platinum with cobalt and nickel being particularly preferred. The Group VIB metals consist of chromium, molybdenum and tungsten, with molybdenum and tungsten being particularly preferred. The metallic components are supported on a porous carrier material. The carrier material may comprise alumina, clay or silica. Particularly useful catalysts are those containing a combination of cobalt or nickel metals ranging from 2.0 to 5 wt % and from 5 to 15 wt % molybdenum on an alumina support. The weight percentages of the metals are calculated as though they existed in the metallic state. Typical commercial catalysts comprise spherical or extruded alumina based composites impregnated with Co—Mo or Ni—Mo in the proportions suggested above. Other useful catalyst compositions comprise 15 to 20 wt. % nickel on alumina. The ABD of commercial catalysts generally range from 0.5 to 0.9 g/cc with surface areas ranging from 150 to 250 $m^2$/g. Generally, the higher the metals content on the catalyst, the more active the catalyst.

Effluent from the saturation zone is separated to provide the recycle stream of heavy paraffins. The heavy paraffin components comprise the product hydrocarbons. Separation of the recycle stream may take place in a simple separator that performs a rough cut of the saturation effluent to provide enough heavy material for recycle to the oligomerization zone and any quench material that circulates through the saturation zone. Alternately the recycle may comprise a side stream of product after fractionation from lighter materials in a primary separator.

Preferably, effluent from the saturation reaction zone enters a quench separator. The quench separator divides a high proportion of the C4 and lower boiling materials from the saturation zone effluent to provide a quench stream with a relatively higher concentration of C7 and heavier hydrocarbons. The recovery of the higher molecular weight material from the effluent of the saturation reaction zone benefits the integration of the oligomerization reaction zone and the saturation reaction zone. The recycle of the C7 and heavier hydrocarbons provides a non-reactive stream that permits a liquid concentration to be maintained in the oligomerization reaction zone at lower pressures.

The lower pressure oligomerization zone operation which may be obtained by the use of this invention may also be used to beneficially integrate a dehydrogenation zone upstream of the oligomerization zone. Typical feeds to a dehydrogenation zone will comprise light paraffin streams. Preferred feeds are rich in $C_4$ paraffins and contain a high percentage of isobutane. (The term rich when used herein means a stream having a weight or volume percent content of at least 50% of the mentioned component while the term relatively rich means a stream having a higher concentration of the mentioned component than the feed from which it was derived.) Feeds for the dehydrogenation zone will more preferably have an isobutane concentration in a range of from 60 to 99 wt %. Typical sources for this feedstream are field butanes, refinery C4 saturate streams, and butanes from gas recovery units. The isobutane stream can be obtained from refinery butane streams or other sources that will provide a butane rich feed. Preferred dehydrogenation reaction zones for this invention beneficially integrate the dehydrogenation zone with the oligomerization reaction zone by the use of high pressure and low conversion conditions. The lower conversion will reduce catalyst deactivation and, particularly when combined with higher space velocity, will allow most dehydrogenation reaction zones to operate with reduced regeneration requirements. In addition, higher pressure conditions in particular reduce compression requirements for effluent separation and improve process efficiency.

Catalytic dehydrogenation process and reactor arrangements are well known. Suitable dehydrogenation processes will admix a feedstock with a stream comprising hydrogen and contact the feed with catalyst in a reaction zone. The preferred feedstocks for catalytic dehydrogenation of this invention predominately comprise isobutane and may also contain propane and pentanes. The catalytic dehydrogenation process will treat the substantially paraffinic hydrocarbons to thereby form olefinic hydrocarbon compounds. Suitable dehydrogenation zones for this process provide a low conversion of isobutane to isobutene with a relatively low rate of catalyst fouling.

Any suitable dehydrogenation catalyst may be used in the process of the present invention. The particular dehydrogenation reactor configuration will depend on the performance characteristics of the catalyst and the reaction zone. Low conversion conditions for the operation of the dehydrogenation zone will usually produce olefin yields in a range of 10 to 40 wt % and more typically in a range of from 20 to 30 wt %. Operating conditions within the dehydrogenation zone are preferably chosen to produce an olefin effluent stream having an isobutene to normal butene and propylene ratio of more than 1. Regeneration of the catalyst can be accomplished by a swing bed operation, a semi-regeneration operation or a continuous catalyst regeneration section.

A catalytic dehydrogenation reaction is normally effected in the presence of catalyst particles comprised of one or more Group VIII nobel metals (e.g., platinum, iridium, rhodium, palladium) combined with a porous carrier, such as a refractory inorganic oxide. Generally, the preferred catalyst comprises a platinum group metal component, an alkali metal component with the porous carrier. The catalyst may also contain promoter metals which advantageously improve the performance of the catalyst. It is preferable that the porous carrier material of the dehydrogenation catalyst be an absorptive high surface area support having a surface area of about 25 to about 500 m$^2$/g. The porous carrier material should be relatively refractory to the conditions utilized in the reaction zone and may be chosen from those carrier materials which have traditionally been utilized in dual function hydrocarbon conversion catalysts. A porous carrier material may therefore be chosen from an activated carbon, coke or charcoal, silica or silica gel, clays and silicates including those synthetically prepared and naturally occurring, which may or may not be acid-treated as, for example, attapulgus clay, diatomaceous earth, kieselguhr, bauxite; refractory inorganic oxide such as alumina, titanium dioxide, zirconium dioxides, magnesia, silica alumina, alumina boria; crystalline alumina silicates such as naturally occurring or synthetically prepared mordenite or a combination of one or more of these materials. The preferred porous carrier material is a refractory inorganic oxide, with the best results being obtained with an alumina carrier material. Alumina is the most commonly used carrier. The preferred alumina materials are known as the gamma, eta and theta alumina with gamma and theta alumina giving the best results. The preferred catalyst will have a theta alumina carrier which is in the form of spherical particles. Particles having relatively small diameters on the order of about 1/16" are preferred, but the particles may be as large as 1/4".

Of the platinum group metals, which include palladium, rhodium, ruthenium, osmium or iridium, the use of platinum is preferred. The platinum group component may exist within the final catalyst composite as a compound such as an oxide, sulfide, halide, oxysulfide, etc., of an elemental metal or in combination with one or more other ingredients of the catalyst. It is believed that the best results are obtained when substantially all of the platinum group components exist in the elemental state. The platinum group components generally comprises from about 0.01 to about 2 wt. % of the final catalytic composite, calculated on an elemental basis. It is preferred that the platinum content of the catalyst be between about 0.2 and 1 wt %. The preferred platinum group component is platinum, with palladium being the next preferred metal. The platinum group component may be incorporated into the catalyst composite in any suitable manner such as by coprecipitation or cogelation with the preferred carrier material, or by ion-exchange or impregnation of the carrier material. The preferred method of preparing the catalyst normally involves the utilization of a water-soluble decomposable compound of a platinum group metal to impregnate the calcined carrier material. For example, the platinum group component may be added to the support by commingling the support with an aqueous solution of chloroplatinum or chloropalladic acid. An acid such as hydrogen chloride is generally added to the impregnation solution to aid in the distribution of the platinum group component throughout the carrier material. Preferred catalyst materials will have a chloride concentration of from 0.5 to 3 weight percent.

The preferred alkali metal is normally either potassium or lithium, depending on the feed hydrocarbon. The concentration of the alkali metal may range from about 0.1 to 3.5 wt %, but is preferably between 0.2 and about 2.5 wt % calculated on an elemental basis. This component may be added to the catalyst by the methods described above as a separate step or simultaneously with the solution of another component.

As noted previously, the dehydrogenation catalyst may also contain a promoter metal. One such preferred promoter metal is tin. The tin component should constitute about 0.01 to about 1 wt % tin. It is preferred that the atomic ratio of tin to platinum be between 1:1 and about 6:1. The tin component may be incorporated into the catalytic composite in any suitable manner known to effectively disperse this component in a very uniform manner throughout the carrier material. A preferred method of incorporating the tin component involves coprecipitation during the preparation of the preferred carrier material. A more detailed description of the preparation of the carrier material and the addition of platinum component and the tin component to the carrier material may be obtained by reference to U.S. Pat. No. 3,745,112.

The low severity operation of the preferred dehydrogenation zones will result in an extended catalyst life. Depending on the catalyst system and the properties of the dehydrogenation zone feed, the dehydrogenation reaction zone will use a solid catalyst that can operate as a fixed bed, a semi-regenerated bed or continuous catalyst regeneration. The actual arrangement of the dehydrogenation zone may be relatively simple and include a single reactor and single heater. Moreover, the dehydrogenation catalytic reaction zone may consist of multiple catalyst beds. In one such system, the catalyst is employed within an annular bed through which it is movable via gravity flow. Preferred methods of dehydrogenating light hydrocarbons, suitable for the continuous dehydrogenation of isobutane using a continuous catalyst regeneration system are described in U.S. Pat. Nos. 5,227,566, 3,978,150, 3,856,662, 3,854,887, 3,839,197, 3,825,116, and 3,706,536 the contents of which are hereby incorporated by reference.

In preferred form, the dehydrogenation process will employ a moving bed reaction zone and regeneration zone. Moving bed systems advantageously maintain production while the catalyst is removed or replaced. In a typical moving bed reaction zone fresh catalyst particles are fed through the reaction zones by gravity. Catalyst is withdrawn from the bottom of the reaction zone and transported to a regeneration zone where a hereinafter described multi-step regeneration process is used to recondition the catalyst to restore its full reaction promoting ability. Catalyst flows by gravity through the various regeneration steps and then is withdrawn from the regeneration zone and furnished to the reaction zone. The arrangement of typical combustion, drying and redispersion section in a moving bed may be seen in U.S. Pat. Nos. 3,653,231 and 5,227,566 the contents of which are hereby incorporated by reference.

Operating conditions for the preferred dehydrogenation zone of this invention will usually include an operating temperature in the range of from 950° to 1200° F. with an operating temperature of at least 1100° F. being preferred and with an operating temperature of about 1130° F. being particularly preferred. A relatively high operating pressure characterizes the low conversion conditions of the preferred dehydrogenation zone and is usually within a range of 40 to 150 psig. Pressures for the preferred dehydrogenation zone are more typically at least 50 psig with pressures of about 70 to 110 psig being particularly preferred. Low conversion conditions will also permit the operation of the dehydrogenation zone at low hydrogen to hydrocarbon ratios in a range of from 0.1 to 4 and more preferably about 0.2. Space velocities for the dehydrogenation zone range from 0.5 to 50 and will normally exceed 10 and typically equal about 15.

Low conversion and lower pressures for the dehydrogenation reaction zone also promote savings in equipment when integrated with a low pressure oligomerization zone of this invention. For example a reciprocating compressor may be used in the recovery of recycle hydrogen from the dehydrogenation effluent. Higher pressures within the dehydrogenation zone and its integration with the saturation reaction zone also reduces the equipment expense associated with hydrogen supply and recovery. Use of relatively high pressures within the dehydrogenation zone can also result in the recovery of a hydrogen stream having purities of 80% or greater with minimal cooling. The low conversion operation of the dehydrogenation zone allows utilization of such a low purity hydrogen stream due to the high amount of isobutane recycle that dilutes the harmful effect of any olefin carryover to the dehydrogenation zone. In addition, the supply of the excess hydrogen from the dehydrogenation zone to the saturation zone results in the recovery of excess isobutane in the primary fractionator which would otherwise pose an unacceptable loss of such hydrocarbons in the operation of the process.

The process and different operational steps will be described in conjunction with the figure. The figure shows only one form of the invention and only those portions of the process that are necessary to gain an understanding of the invention and the necessary means of integrating the principal processing steps that comprise the invention. Further details related to valves, control means, pumps, compressors, coolers, and other necessary processing equipment are well known to those skilled in the art and not described in detail unless necessary for an understanding of the invention.

A light hydrocarbon stream, rich in $C_4$ paraffins enters a deisobutanizer column 10 via a line 12. Column 10 also receives recycle material from a hereinafter described saturation zone effluent stream via a line 96. Deisobutanizer column 10 provides a sidecut stream 16 that comprises feedstream isobutane for a dehydrogenation zone.

Line 16 passes the dehydrogenation zone feed through exchanger 98. Heating continues as line 16 first passes the dehydrogenation zone feed through exchanger 18 to recover heat from the dehydrogenation zone effluent 20. Depending on the composition of the dehydrogenation catalyst a small amount of sulfur may be added via line 17 to prevent carbon formation on metallic surfaces of the reactors and heaters and to passivate the catalyst. Line 22 combines the dehydrogenation zone feedstream with a hydrogen-containing stream to produce a combined feedstream that passes via line 28 through charge heater 24 and into a dehydrogenation reactor 26. Contact with a dehydrogenation catalyst dehydrogenates a portion of the paraffin components from the feedstream which pass out of dehydrogenation zone reactor 26 via a line 30 and through an inter-heater 32 to provide heat of reaction for further conversion of isobutane in a second reactor 34. Line 36 carries the heated and partially converted dehydrogenation zone feed through reactor 34 and out of the reactor through effluent stream 20.

The figure schematically shows the operation of the dehydrogenation zone with a catalyst regeneration system that supplies regenerated catalyst to reactors 26 and 34 via line 38. A catalyst transfer system (not shown) transfers coked catalyst from the bottoms of reactor 26 and 34 via conduits 42 and 44 respectively and into a catalyst lift conduit 46. Conduit 46 delivers the coked catalyst to a regeneration section 48. Catalyst regeneration section 48 reconditions catalyst by coke combustion.

The effluent stream 20 from the dehydrogenation reaction zone contains at least hydrogen, butane, butenes, some light hydrocarbons and small amounts of heavy hydrocarbons. Line 20 passes the effluent from the dehydrogenation reaction zone through exchanger 18 and into a separator 52 to remove the various heavy hydrocarbon components from the effluent stream via line 57. A line 56 carries the vapor effluent from heavies separator 52 to a hydrogen separator 54 for the recovery of a hydrogen-containing stream that recycles hydrogen to the dehydrogenation zone feed via line 22. The dehydrogenation zone of this invention may operate with a relatively impure hydrogen stream. A suitable hydrogen recycle stream for this invention may have a hydrogen concentration of less than 90 wt %. Acceptable hydrogen concentrations may be as low as 70 wt %, and more typically about 80 wt %, with the remainder of the hydrogen-containing stream comprising $C_1$–$C_3$ hydrocarbons and typically some small concentrations of $C_4$ hydrocarbons. The purity of the hydrogen stream to the dehydrogenation zone may be increased if desired by chilling the overhead from separator 54 to decrease the carry over of impurities into stream 22. The remainder of the hydrogen-containing stream recovered from separator 54 serves as a hydrogen feed to the saturation reactor as hereinafter described.

The bottom stream from separator 54 is combined with an olefin-containing stream 58 to provide a combined feed to the oligomerization reaction zone. The olefin-containing stream carried by line 58 supplies additional olefins to the oligomerization reaction zone. The olefins entering through line 58 will include normal butenes and isobutene and may also include $C_3$ and $C_5$ olefins as well some paraffins.

A line 60 carries the combined oligomerization zone feedstream through an exchanger 62 to heat the oligomerization feed against the saturation zone effluent. Line 64 carries the heated oligomerization feed through a trim heater 66 and to the reactors via a line 68. In accordance with this invention a heavy recycle stream comprising $C_7$ and heavier paraffins is combined with the feed to the oligomerization zone via line 69. Oligomerization feed passes serially through a series of oligomerization reactors 70 which are divided into multiple stages. Additional $C_7$ and heavier paraffins enter inter-bed locations in reactors 70 via quench distribution lines 72 to supply quench to each internal reaction stage. The injection of the quench provides the heavy material of this invention to also provide the advantages of catalyst flushing and selectivity to high octane $C_8$ isomers. Effluent piping 74, connected to the outlet of the oligomerization reactor 70, recovers an oligomerization effluent stream.

A line 76 supplies hydrogen to the effluent from the oligomerization reaction zone to produce a combined feed for the saturation reaction zone. Line 76 receives hydrogen from the dehydrogenation process via lines 78 and 80. Any outside make-up hydrogen enters the process via a line 82. Preferably all of the effluent from the added hydrogen, directly together with the added hydrogen, directly into a saturation zone.

The saturation zone saturates the unsaturated gasoline boiling range components and unreacted light olefins from the oligomerization zone to provide an alkylate quality product stream. The saturation zone will typically use a plurality of reactors 82, 86 arranged in series with feed passing through each reactor. The series reactor arrangement permits control of temperatures.

Line 84 carries the combined feed in indirect heat exchange against the effluent from the saturation zone in exchanger 86 and the heated saturation zone feed flows via a line 87 into the first saturation reactor 82. The preferred arrangement of the hydrogenation zone will be a two stage hydrotreating reactor system wherein the effluent from the first saturation reactor 82 passes via a line a 85 into a second reaction zone 86. To control the temperature exotherm from the first reaction zone a portion of the heavy hydrocarbons pass as a quench stream via line 88 into combination with the first reaction zone effluent 85. The now saturated oligomerization reaction zone effluent passes via line 90 through heat exchanger 86 and via line 91 to a heat exchanger 62 to recover heat from the saturation reaction before entering a quench separator 92 via a line 93.

Quench separator 92 recovers saturated heavy material from the saturation zone to provide the liquid phase recycle stream of this invention. The bottom stream 94 from separator 92 supplies the heavy recycle material to the oligomerization zone via lines 69 and 72 and the quench to the saturation reaction zone via line 88. The remainder of the heavy material is returned to the separator overhead via line 95 for withdrawal from the process as bottoms product from the deisobutanizer 10. The overhead material from separator 92 and any additional separator bottoms supplied by line 95 are taken by line 96 and contain primarily alkylate quality product and unreacted butanes. Additional heat recovery from the separator stream 96 takes place in exchanger 98 to initially raise the temperature of the dehydrogenation zone input stream from deisobutanizer 10.

The preferred arrangement of this invention uses deisobutanizer 10 to perform a simultaneous distillation of the product containing separator overhead stream along with the initial production of the dehydrogenation zone feed stream. The preferred deisobutanizer vessel separates off the light ends as an overhead stream 100 while simultaneously supplying the previously described dehydrogenation zone feed 16 as a sidecut. The deisobutanizer column design is arranged to provide a high concentration of the isobutanes in the feed to the dehydrogenation zone via the sidecut stream. The deisobutanizer will typically provide an isobutane purity of 80 wt % and more preferably at least 95 wt %. The column also operates to separate remaining $C_4$ minus materials from the dehydrogenation zone feedstream via overhead stream 100. The primary fractionator also delivers the saturated oligomerization zone product components as a bottom stream 102. The deisobutanizer of this preferred arrangement may also supply a normal $C_4$ sidecut stream to withdraw excess unreacted butanes from the process. The sidecut is, withdrawn via a line 104 which may supply additional heat by indirect heat exchange with the $C_4$ input stream in a heat exchanger 106.

To more fully demonstrate the attendant advantages of the present invention, the following tests were performed.

EXAMPLE 1

A feedstream having a composition of 13 wt % normal butene, 17.7 wt % isobutene and 69.4 wt % isobutane was contacted with about 50 cc of a solid phosphoric acid catalyst comprising a calcined mixture of phosphoric acid in siliceous base. The catalyst comprised pellets approximately ¼" in diameter and length that were retained in a ⅞" steel reactor vessel having a volume of 70 cc. Channeling was avoided by carefully sand packing the void volume between particles. The feed entered the reactor at a temperature of 374° F. and a pressure of 500 psig and passed through the reactor at a liquid hourly space velocity of 2. The oligomerization reaction produced a maximum reactor temperature of 396° F. A sample of the reactor effluent was recovered, distilled and analyzed to determine the conversion of $C_4$ olefins and the carbon number selectivities of the products. The results of the analysis are shown in Table 1.

TABLE 1

| FEED | CONV. % | CARBON NO. SELECTIVITIES, WT % | | | | |
|---|---|---|---|---|---|---|
| | | 5→7 | 8 | 9→11 | 12 | >12 |
| EXAMPLE 1 | n-$C_4^-$ = 85 iso-$C_4^-$ = 91 TOTAL $C_4^-$ = 88 | 8.4 | 56 | 5.2 | 28 | 2.4 |
| EXAMPLE 2 | n-$C_4^-$ = 81 iso-$C_4^-$ = 91 TOTAL $C_4^-$ = 86 | 4.7 | 66.2 | 3.9 | 24.6 | 0.6 |

EXAMPLE 2

In order to demonstrate the advantages of a heavy recycle an additional 25 wt % of normal $C_8$ paraffins were added to the feed of Example 1 and run at the operating conditions and with the same catalyst as Example 1. The oligomerization zone reached a maximum temperature of 392° F. A sample of the effluent from the reaction zone was again distilled and analyzed and found to contain a significantly higher percentage of $C_8$ olefins. The results of the analysis are again shown in Table 1.

Comparison of Examples 1 and 2 demonstrates that at approximately equal $C_4$ olefin conversions the addition of the $C_8$ paraffins shifted the selectivity of the reactor effluent significantly toward the production of the highly desired $C_8$ isomer and surprisingly away from the production of both higher and lower carbon number isomers.

As this example demonstrates, the recycle stream of this invention provides a significant improvement in the selectivity of the oligomerization to high octane $C_8$ isomers.

EXAMPLE 3

A feedstream having a composition of 8.4 wt % normal butene, 21.9 wt % isobutene and 69.7 wt % isobutane was contacted with about 50 cc of a solid phosphoric acid catalyst of the type used in Examples 1 and 2. The reactor vessel and catalyst loading technique was also of the same type used in Examples 1 and 2. Feed entered the reactor at a temperature of 376° F. and a pressure of 500 psig and passed through the reactor at a liquid hourly space velocity of 2. The oligomerization reaction produced a maximum reactor temperature of about 403° F. A sample of the reactor effluent was recovered hydrogenated, distilled and analyzed to determine the conversion of $C_4$ olefin, the carbon number selectivities of the products and the research and motor octane numbers. The results of the analysis are shown in Table 2.

EXAMPLE 4–6

In order to demonstrate the advantages of a heavier components than $C_8$ and lower operating temperatures an additional 25 wt % of normal $C_{12}$ paraffins were added to the feed of Example 3 and run at a range of reduced operating temperatures and space velocities with the same catalyst as Example 3. Conversions, selectivity and research and motor octane numbers after distillation and hydrogenation of effluents from the three runs with the added $C_{12}$ components to the feed are shown in Table 2 as Examples 4–6.

Examples 4 and 5 both demonstrate a much higher selectivity to $C_8$ isomers than Example 3 at an only slightly reduced conversion. The improved selectivity resulted in a much higher octane number than that obtained without the $C_{12}$ components in Example 3. Example 6 demonstrates that higher conversions than Example 3 may be obtained at relatively higher temperatures and a reduced space velocity while still maintaining a significantly higher selectivity to $C_8$ isomers than shown in Example 3.

What is claimed is:

1. A process for the production of saturated oligomers having a high octane rating, said process comprising:
    a) passing an oligomerization zone feed comprising $C_3$ to $C_5$ olefins and $C_3$ to $C_5$ paraffins at oligomerization conditions into contact with an oligomerization catalyst at oligomerization conditions
    b) passing a recycle stream comprising paraffins having a carbon number of 8 to 12 into contact with said catalyst;
    c) recovering an oligomerization effluent comprising said paraffins and olefins having a carbon number of at least 7;
    d) passing at least a portion of the effluent from the oligomerization zone and a hydrogen containing stream into a saturation zone and contacting said oligomerization zone effluent and hydrogen with a saturation catalyst at saturation conditions to saturate olefins in said oligomerization effluent and recovering a saturation zone effluent stream;
    e) passing a portion of said saturation zone effluent stream comprising paraffinic hydrocarbons having 8 to 12 carbon atoms to said oligomerization zone as said recycle stream; and,
    f) recovering a portion of said saturation zone effluent stream comprising $C_8$ and heavier paraffins.

2. The process of claim 1 wherein said oligomerization zone catalyst comprises a solid phosphoric acid catalyst.

3. The process of claim 1 wherein said oligomerization zone operates at a pressure of less than 300 psig.

4. The process of claim 1 wherein at least a portion of said recycle stream enters said oligomerization zone with the feed.

5. The process of claim 1 wherein said feed comprises at least a portion of the effluent from a dehydrogenation zone.

TABLE 2

| FEED | TEMP °F. INLET/MAX | LHSV, HRS$^{-1}$ | CONV. % | CARBON NO. SELECTIVITIES, WT % | | | | | RON | MON |
| --- | --- | --- | --- | --- | --- | --- | --- | --- | --- | --- |
| | | | | 5→7 | 8 | 9→11 | 12 | >12 | | |
| EXAMPLE 3 | 376/403 | 2 | n-$C_4^-$ = 83<br>iso-$C_4^-$ = 94<br>TOTAL $C_4^-$ = 91 | 10.5 | 51 | 6 | 30 | 2.5 | 83.3 | 84.6 |
| EXAMPLE 4 | 308/322 | 2 | n-$C_4^-$ = 54.5<br>iso-$C_4^-$ = 96.5<br>TOTAL $C_4^-$ = 87 | 0.8 | 87.2 | 0.3 | 11.7 | — | 101 | 95.0 |
| EXAMPLE 5 | 320/340 | 2 | n-$C_4^-$ = 63.7<br>iso-$C_4^-$ = 95.9<br>TOTAL $C_4^-$ = 88.7 | 1.3 | 83.1 | 0.9 | 14.7 | — | 99.7 | 94.7 |
| EXAMPLE 6 | 329/338 | 0.75 | n-$C_4^-$ = 83<br>iso-$C_4^-$ = 96.5<br>TOTAL $C_4^-$ = 94 | 2.3 | 75.3 | 1.6 | 20.8 | — | 97.9 | 93.2 |

All three of the runs operated with reduced temperatures relative to Example 3 and show significant improvement to the $C_8$ selectivity by the addition of the normal $C_{12}$ paraffins.

6. The process of claim 1 wherein said feed stream comprises $C_4$ olefins.

7. The process of claim 1 wherein at least a portion of said saturation zone effluent is cooled and returned to said oligomerization zone and said saturation zone as a quench liquid that supplies a portion of said recycle stream.

8. The process of claim 7 wherein said oligomerization zone contains a bed of solid phosphoric acid catalyst and said quench liquid is injected into said bed at at least one intermediate location.

9. The process of claim 1 wherein said saturation zone comprises a hydrotreater.

10. The process of claim 1 wherein said oligomerization zone operates at temperature of from 300° to 400° F.

11. A process for the production of a high octane motor fuel product from an isobutane containing input stream, said process comprising:
   a) passing said input stream comprising isobutane to a dehydrogenation zone and contacting said input stream in said dehydrogenation zone with a dehydrogenation catalyst at dehydrogenation conditions including a temperature of 950° to 1200° F. and a pressure of 5 to 150 psig and an LHSV of 0.5–50 and recovering hydrogen and a dehydrogenation effluent comprising $C_4$ isoolefins;
   b) separating a hydrogen stream having a hydrogen purity of from 70–95 mol % from said dehydrogenation effluent and recovering a feed stream comprising $C_4$ olefins and $C_4$ paraffins from the remainder of said dehydrogenation effluent to produce an oligomerization zone feed stream;
   c) passing said oligomerization feed and a recycle stream to an oligomerization zone and contacting said oligomerization zone feed with solid oligomerization catalyst at oligomerization conditions including a temperature of 200° to 500° F., a pressure of 100 to 1000 psig, and an LHSV of 0.5 to 5 to recover an oligomerization effluent comprising isoolefins having a carbon number of 8 to 12;
   d) passing the effluent from the oligomerization zone without separation into a saturation zone and said hydrogen stream into said saturation zone and contacting said oligomerization zone effluent and hydrogen with a saturation catalyst at saturation conditions to saturate olefins in the oligomerization effluent and recovering a saturation zone effluent stream;
   e) passing at least a portion of said saturation zone effluent stream to a separation zone to recover a saturated stream comprising paraffins having a carbon number of 8 to 12; and
   f) recycling at least a portion of said saturated stream as said recycle stream.

12. The process of claim 11 wherein the saturation zone comprises a hydrotreater.

13. The process of claim 11 wherein the olefin concentration of the oligomerization zone feedstream is at least 30 wt % isobutene.

14. The process of claim 11 wherein said dehydrogenation zone operates at a pressure of at least 40 psig.

15. The process of claim 11 wherein said first input stream and said saturation zone effluent fraction are recovered from a debutanizer as a sidecut stream and passed to said dehydrogenation zone as a dehydrogenation zone feed.

16. The process of claim 11 wherein said oligomerization zone catalyst comprises a solid phosphoric acid catalyst.

17. The process of claim 11 wherein at least a portion of said saturation zone effluent is cooled and returned to said oligomerization zone and said saturation zone as a quench liquid.

18. The process of claim 17 wherein said oligomerization zone contains a bed of solid phosphoric acid catalyst and said quench liquid is injected into said bed at least one intermediate location.

19. The process of claim 11 wherein said dehydrogenation zone catalyst comprises platinum, tin and potassium metals on an alumina base.

20. The process of claim 11 wherein said dehydrogenation zone operates at a pressure of from 70 to 110 psig.

21. The process of claim 11 wherein said dehydrogenation zone is combined with a hydrogen stream having a hydrogen concentration in a range of from 70 to 90 wt %.

22. The process of claim 11 wherein said solid oligomerization zone comprises multiple beds of a solid phosphoric acid catalyst.

* * * * *